United States Patent [19]

Rapacz et al.

[11] Patent Number: 5,034,332
[45] Date of Patent: Jul. 23, 1991

[54] ASSAY FOR HIGH DENSITY LIPOPROTEIN CHOLESTEROL

[75] Inventors: Jan Rapacz; Judith H. Rapacz, both of Madison, Wis.

[73] Assignee: Wisconsin Alumni Research Foundation, Madison, Wis.

[21] Appl. No.: 563,177

[22] Filed: Aug. 6, 1990

[51] Int. Cl.$^5$ .................... G01N 5/04; G01N 33/48; G01N 33/50

[52] U.S. Cl. ........................... 436/71; 436/63; 435/11

[58] Field of Search ............... 436/60, 63, 71; 435/11

[56] References Cited

FOREIGN PATENT DOCUMENTS 3215310 10/1983 Fed. Rep. of Germany ........ 435/11

OTHER PUBLICATIONS

J. Boursnell et al., 11 J. Reprod. Fert., 139–144 (1966).
J. Boursnell et al., 19 J. Reprod. Fert., 157–166 (1969).
D. Schellpfeffer et al., 23 J. Reprod. Fert., 291–198 (1970).
T. Roberts et al., 41 J. Reprod. Fert., 489–492 (1974).
H. Moore et al., 47 J. Reprod. Fert., 39–45 (1976).
Sigma Diagnostics product information sheet for HDL precipitating reagent, date of publication unknown, admitted prior art.
Chapter 6: "Chemistry Studies," pp. 334–337, in *Cholesterol*, date of publication unknown, admitted prior art.
Sigma Diagnostics pamphlet for Cholesterol Reagent, (1988) by Sigma Chemical Company.

*Primary Examiner*—David L. Lacey
*Assistant Examiner*—David Redding
*Attorney, Agent, or Firm*—Quarles & Brady

[57] ABSTRACT

This invention relates to an assay for high density lipoprotein in blood. More particularly, it relates to the use of boar vesicle seminal plasma protein material to bind to and precipitate HDL cholesterol. In one embodiment, the method involves measuring the cholesterol using standard methods prior to and after precipitation of the HDL. The difference in measurements being an estimate of HDL cholesterol present in the sample.

5 Claims, No Drawings

ASSAY FOR HIGH DENSITY LIPOPROTEIN CHOLESTEROL

This invention was made with United States Government support awarded by the USDA (HATCH Funds). The United States Government has certain rights in this invention.

TECHNICAL FIELD

This invention relates generally to an assay for high density lipoprotein in blood plasma. More particularly, it relates to use of a portion of boar seminal vesicle plasma to estimate levels of plasma HDL.

BACKGROUND ART

Low density lipoprotein ("LDL") and high density lipoprotein ("HDL") are very important components of blood. LDL is involved in transporting cholesterol to the peripheral organs and cells. HDL is involved in transporting cholesterol away from the peripheral organs and cells to the liver. High blood plasma LDL cholesterol levels are correlated with the development of coronary heart disease and heart attacks. On the other hand, high HDL levels appear to reduce the adverse affect of high LDL levels. The ratio of LDL to HDL is therefore now an important predictor for the susceptibility or resistance to coronary heart disease and heart attacks, and as a factor in developing diets.

Precise measurements of HDL lipoprotein levels are therefore highly desirable for clinical purposes. HDL cholesterol is currently usually determined by first measuring total blood plasma cholesterol, then LDL is precipitated out, and then the level of total cholesterol left in the supernatant is measured. The difference is assumed to be HDL. While deducing HDL in this way gives a rough estimate, it assumes that there is no other type of cholesterol present in the sample, and the method is limited by the ability of the LDL precipitant to selectively and effectively pull the LDL out of solution. There are currently no better practical methods to assay levels of HDL cholesterol (albeit there is also an ultracentrafuge method which is very costly and time consuming). The development of a more practical method for directly measuring HDL cholesterol is therefore highly desirable.

In separate unrelated work a red blood cell haemagglutinating factor has been isolated in boar seminal plasma. See J. Boursnell et al., 11 J. Reprod. Fert. 139-144 (1966). It is present in boar vesicular secretion, but not in epididymal seminal plasma or in boar spermatozoa. See also J. Boursnell et al., 19 J. Reprod. Fert. 157-266 (1969) (protein H in factor agglutinates sperm cells); H. Moore et al., 47 J. Reprod. Fert. 39-45 (1976) (factor secreted by seminal vesicle accessory gland); D. Schellpfeffer et al., 23 J. Reprod. Fert. 291-98 (1970) (two sizes of proteins active in factor); T. Roberts et al., 41 J. Reprod. Fert. 489-92 (1974) (lipid site on red blood cell may cause agglutination). The disclosure of these articles and of all other articles recited herein are incorporated by reference as if fully set forth herein. While there has been some interest in studying this factor and whether it contains any lipoprotein, to date there has been no suggestion in the art that this factor has any utility vis a vis testing for HDL levels.

DISCLOSURE OF THE INVENTION

In one embodiment, the invention provides an assay for the presence of HDL cholesterol in a sample. One mixes the sample with a proteinaceous material that is also present in boar vesicle plasma so as to cause a precipitation of HDL cholesterol bound to the proteinaceous material. Preferably, prior to the mixing step the total amount of cholesterol in the sample has been measured and after the mixing step the amount of cholesterol left in the supernatant that is formed during the mixing step is measured. The preferred proteinaceous material is "protein H" in J. Bouisnell et al., 19 J. Reprod. Fert. 157-266 (1969).

In another form, the invention provides a kit for determining the presence of HDL cholesterol in a sample. The kit has a proteinaceous material that is also present in boar vesicle plasma, and an anti-protease enzyme factor (such as EDTA or citrate) which stabilizes the vesicle plasma. If desired the kit can also contain HDL cholesterol (which will serve as a control).

It will be appreciated that if human or other animal blood is spun down in a centrifuge in a conventional manner to separate out the red blood cells, and the remaining blood plasma is mixed with the boar vesicle plasma, the HDL cholesterol will be selectively precipitated out of the plasma. One can either compare the total cholesterol before the mixing step with that remaining after separating out the supernatant from the precipitant, or weigh or otherwise compare the amount of precipitant against precipitants from controls with known HDL levels.

The objects of the present invention therefore include:
providing assays and kits of the above kind; and
providing assays and kits which enable a rapid and low cost measurement of HDL cholesterol.

BEST MODES FOR CARRYING OUT THE INVENTION

A. Materials

Young boars (6 months of age) were sacrificed to remove intact their sexual accessory vesicle gland and obtain unmixed fluid. The glands are split open and drained. The fluid is centrifuged and the supernatant is kept. It is then mixed with 10% EDTA solution at a ratio of 1 ml EDTA to 100 ml plasma. The EDTA acts as an anti-coagulant and an anti-protease enzyme factor. Instead of EDTA, one can use citrate or other antiproteases for this purpose. The solution is preferably stored at 4° C.

A specimen of human (or other animal) blood plasma can be prepared by centrifuging it to spin down red blood cells using standard clinical techniques. The plasma supernatant is taken off and used for the test.

B. Specificity

Immunoelectrophoresis in agar gel was chosen as method to confirm the specificity of the precipitating activity. Under standard electrical current typically used to separate blood plasma proteins, the precipitinogen of the swine plasma was located mainly in the alpha ($\alpha$) high density position, and extended only slightly into the beta ($\beta$) low density position. This was determined by comparing the electrophoretic mobility of the detected precipitinogen with migrations of known swine plasma proteins. The closest resemblance appeared with apolipoprotein AI, known to be the primary structural constituent of high density lipoprotein (HDL).

Assay

As an example, a sample of the blood plasma is first tested for total cholesterol. One way of doing this is the peroxidase color method of Sigma Chemical Company as described in their pamphlet "Sigma Diagnostics — The Standard Source — Cholesterol" (1988). In this type of procedure, cholesterol esters are first hydrolyzed by cholesterol esterase to cholesterol. The cholesterol produced by hydrolysis is oxidized by cholesterol oxidase to cholest-4-en-3-one and hydrogen peroxide ($H_2O_2$). The hydrogen peroxide produced is then coupled with a chromogen, 4-aminoantipyrine and p-hydroxybenzene-sulfonate in the presence of peroxidase to yield a quinoneimine dye which has an absorbance maximum of 500 nm. The intensity of the color produced is directly proportional to the cholesterol concentration in the sample.

To determine HDL using the present invention, then takes another portion of the plasma and in a centrifuge adds 400 $\mu$l of plasma and 50 $\mu$l of the boar vesicle plasma (at 20° C.). After mixing, one centrifuges 2000×g for 10–15 minutes to obtain clear supernatant. A sample of the supernatant is then retested using the above procedure. The difference between the two readings (with appropriate corrections for dilutions made) is HDL. If desired, as an alternative the 100 $\mu$l of blood plasma can be mixed with 100 $\mu$l of the EDTA boar vesicle plasma solution.

It should be appreciated that the invention is not limited to the preferred embodiments. For example, the precipitant can be dried and then weighed, the weight then being compared against control HDL precipitant results. Also, it is expected that optimal mixtures of the boar proteinaceous material that conveys this property will soon be identified, and that this material will at some point be able to be artificially synthesized. Also, the term "boar" is intended to broadly cover male swine, male pigs, and male hogs. Thus, the claims should be referred to in assessing the full breadth of the invention.

We claim:

1. An assay for the presence of HDL cholesterol in a blood plasma sample, comprising the steps of:
    mixing the sample with a proteinaceous material that is also present in protein H of boar vesicle seminal plasma so as to cause a precipitation of HDL cholesterol bound to the proteinaceous material; and
    measuring either the amount of cholesterol in a supernatant formed by the mixing step, or the amount of precipitant formed in the mixing step.

2. The assay of claim 1, where the sample is human blood plasma.

3. The assay of claim 2, wherein prior to the mixing step the amount of cholesterol in the sample is measured.

4. The assay of claim 3, wherein after the mixing step the amount of cholesterol in a supernatant formed by the mixing step is measured.

5. The assay of claim 1, wherein EDTA is present during the mixing step.

* * * * *